United States Patent
Takacs et al.

(10) Patent No.: US 8,512,959 B2
(45) Date of Patent: Aug. 20, 2013

(54) MONOCLONAL ANTIBODY BASED BIOMARKER DISCOVERY AND DEVELOPMENT PLATFORM

(75) Inventors: Laszlo Takacs, Newbury Park, CA (US); Andras Guttman, San Diego, CA (US); William S. Hancock, Brookline, MA (US); Barry L. Karger, Newton, MA (US); Manuel Duval, New London, CT (US); Patrick Berna, Gaillon (FR)

(73) Assignee: Northwestern University, Boston, MA (US)

( * ) Notice: Subject to any disclaimer, the term of this patent is extended or adjusted under 35 U.S.C. 154(b) by 1216 days.

(21) Appl. No.: 10/588,392

(22) PCT Filed: Feb. 9, 2005

(86) PCT No.: PCT/US2005/004484
§ 371 (c)(1), (2), (4) Date: Aug. 3, 2006

(87) PCT Pub. No.: WO2005/077106
PCT Pub. Date: Aug. 25, 2005

(65) Prior Publication Data
US 2007/0172887 A1 Jul. 26, 2007

Related U.S. Application Data

(60) Provisional application No. 60/543,004, filed on Feb. 9, 2004.

(51) Int. Cl.
*G01N 33/53* (2006.01)
(52) U.S. Cl.
USPC .............. 435/7.1; 436/538; 436/548; 514/1.1
(58) Field of Classification Search
None
See application file for complete search history.

(56) References Cited

U.S. PATENT DOCUMENTS

| | | | |
|---|---|---|---|
| 5,242,799 A | 9/1993 | Samuel et al. | 435/7.1 |
| 5,652,138 A * | 7/1997 | Burton et al. | 435/252.33 |
| 6,887,687 B2 * | 5/2005 | Anderson | 435/69.1 |
| 7,396,905 B1 * | 7/2008 | McKeon et al. | 530/350 |
| 2003/0007991 A1 | 1/2003 | Masters et al. | 424/423 |
| 2003/0044849 A1 | 3/2003 | Kessler | |
| 2003/0224436 A1 | 12/2003 | Nelson | |
| 2003/0228291 A1 | 12/2003 | Lawman et al. | 424/93.21 |
| 2005/0009118 A1 * | 1/2005 | Zhang | 435/7.23 |

FOREIGN PATENT DOCUMENTS

| | | |
|---|---|---|
| WO | WO 99/39204 | 8/1999 |
| WO | WO 03/028625 A | 4/2003 |

OTHER PUBLICATIONS

Hoogenboom et al., Immunotechnology, 4:1-20 (1998).*
Andersen et al., PNAS, 93:1820-1824 (1996).*
Nagai et al., Biochemical Society Transactions, 31(part 6):1438-1440 (2003).*
Conze et al., Ann. N.Y. Acad. Sci., 996:222-226 (2003).*

* cited by examiner

*Primary Examiner* — Jim Ketter
(74) *Attorney, Agent, or Firm* — McLane, Graf, Raulerson & Middleton, PA

(57) ABSTRACT

A method or platform for monoclonal antibody based biomarker discovery is disclosed. The method according to the invention provides for the integration of analyte collection, hybridoma screening and nanovolume integrated mass spectrometry (NVIMS) to achieve a robust screening system that is capable, for example, of cutting 4-6 years off of the classical biomarker discovery and development process. The invention provides a platform for the rapid, high-throughput production, isolation and characterization of, e.g., disease specific biomarkers together with highly specific monoclonal antibodies. The method of the invention has a variety of applications such as, but not limited to, drug testing, biohazard applications, ecological applications, physiological applications and/or pathology screening applications. The method of the invention is also capable of being performed or used as or with a high-throughput screening process or system of the invention.

25 Claims, 8 Drawing Sheets

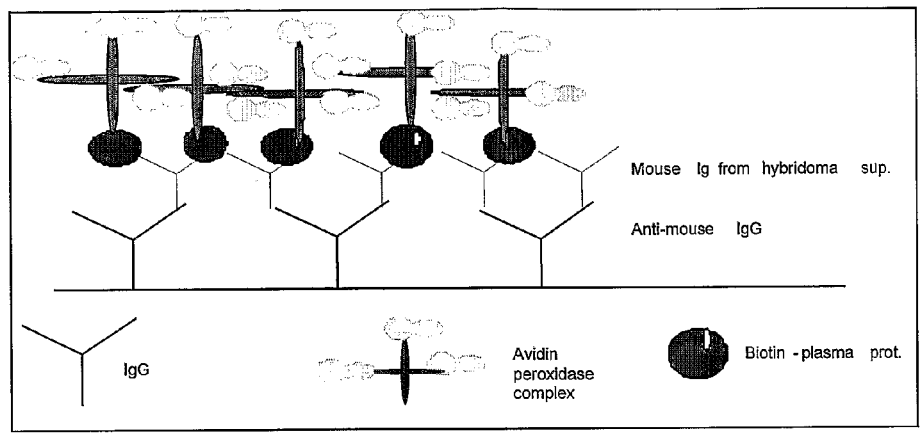
Fig. 2A: ELISA I
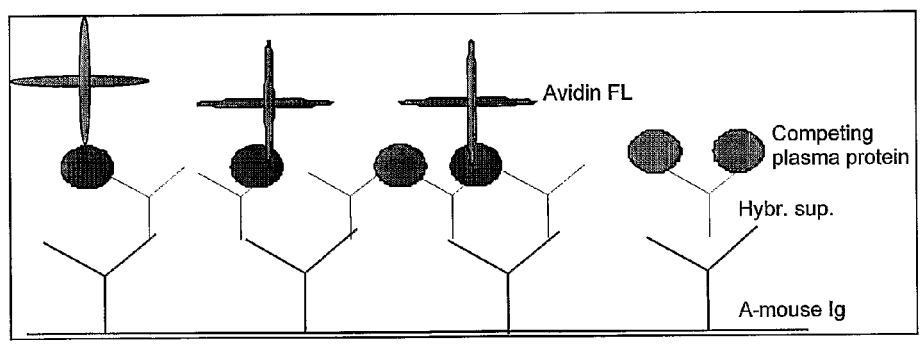
Fig. 2B: ELISA II

MONOCLONAL ANTIBODY BASED BIOMARKER DISCOVERY AND DEVELOPMENT PLATFORM

CROSS REFERENCE TO RELATED APPLICATIONS

This application claims the priority of U.S. Provisional Application No. 60/543,004 filed Feb. 9, 2004 and entitled, MONOCLONAL ANTIBODY BASED BIOMARKER DISCOVERY AND DEVELOPMENT PLATFORM, which is hereby incorporated by reference herein.

BACKGROUND OF THE INVENTION

Biomarkers are surrogate measures of specific changes in biological processes, such as increases or decreases in blood proteins or other analytes, that relate to changes in disease state, or changes in response to drug treatment, environmental components, food, nutrients, etc,. For example, biomarkers as surrogate clinical measures detect early biological responses after drug treatment for analyzing drug safety and early efficacy in testing new drugs. Biomarkers have both prognostic and diagnostic uses. For instance, once the disease status is established, these markers can be used to predict the likely course of the disease and to monitor and assist in the management of disease. One can use biomarkers to stratify diseased populations. Lastly, screening large populations with biomarkers leads to the discrimination of a healthy state from early asymptomatic stages of the disease. Thus, biomarkers can be used for disease management, through diagnosis, staging, stratification and measures of progression and prognosis, and, most importantly, for early measures and/or predictors of drug efficacy or toxicity.

The pharmaceutical industry is interested in biomarker discovery for two main reasons. First, the increasing rate of drug candidate attrition has reached levels where the cost effectiveness of drug discovery and development becomes questionable. The root causes of drug candidate attrition have been identified as resulting from a poor understanding of the mechanism of action of the candidate and from poor pharmacological validation and translation of cellular and animal model-based results to the clinic. The use of biomarkers can bridge the gap between cellular and animal models and human clinical conditions, and new biomarkers, such as HER2, are likely to be relevant to drug mechanisms of action as predictors of drug efficacy. Another major cause of attrition is the individuality of drug toxicity reactions. Identification of individuals with idiosyncratic and other unexpected responses will save lives and money and will allow the introduction of safer drugs. Examples of efficient genetic biomarkers of this type have been reported recently.

Secondly, the high cost of clinical trials for candidate drugs for slowly progressing chronic diseases is prohibitive. Chronic diseases such as Alzheimer disease, type II diabetes, cancer, cardiovascular diseases, rheumatoid arthritis, osteoarthritis and chronic obstructive pulmonary disease represent a major fraction of health care costs and contribute significantly to the direct cause of death. The size of the market and the needs of the public are tremendous in these disease areas, which beg for effective mechanism-based drugs. Yet, the slow, progressive nature of these diseases poses a currently insurmountable problem. The minimal measurable improvement (20-30%) in disease symptoms occurs over such a long period of time that it is impractical and too expensive to test potential therapies in clinical trial settings. The expectation for disease progression-specific biomarkers is that they will permit the prediction of improvement earlier than such improvement actually occurs, thus providing a useful tool to measure and predict the efficacy of novel candidate drugs in shorter and less expensive clinical trials.

SUMMARY OF THE INVENTION

The invention is directed to a method or platform for biomarker discovery that includes the steps of (1) providing a complex analyte as a candidate biomarker source; (2) providing a control sample for said complex analyte; (3) using an aliquot of said complex analyte as an immunogen to generate a population of monoclonal antibodies directed against antigens in said complex analyte; (4) screening said population of monoclonal antibodies directed against antigens in said complex analyte against another aliquot of said complex analyte; (5) screening said population of monoclonal antibodies directed against antigens in said complex analyte against an aliquot of said control sample; and (6) selecting one or more monoclonal antibodies that exhibits a significant difference in binding to an antigen in said complex analyte compared to an antigen in said control sample, whereby the antigen(s) selectively bound by said one or more selected monoclonal antibodies are said biomarker(s).

The term "significant difference" generally refers to or otherwise represents a value (e.g., qualitative or quantitative) that is an indicator of a statistical difference between the reactivity or affinity of a monoclonal antibody to an antigen of a specific complex analyte and the reactivity or affinity of the monoclonal antibody to an antigen of the control sample for that specific complex analyte. For example, a p value less than or approximately equal to 0.05 from either a parametric analysis (e.g., Student's T test or Welch's T test) or a non-parametric analysis (e.g., Wilcoxon-Mann-Whitney test or Kruskal-Wallis test) will, by convention, be an indicator (e.g., a probability indicator) of whether an outcome is statistically different from another outcome and whether such a finding is unlikely due to mere chance.

The following definitions and examples are exemplary and are not intended in any way otherwise to limit the invention. The term "selectively binds" generally refers to a binding reaction of an antibody to an antigen in which the $K_d < 10^{-6}$ M. In one embodiment of the invention, the antigen is identified by methods known to those of skill in the art. The antigen may be, for example, a protein or a peptide, a glycoprotein, a lipid, a glycolipid, a phospholipid, a complex sugar or a nucleic acid.

Complex analytes that can be screened by the method of the invention include any kind of complex mixture. For example, complex analyte mixtures of biological origin can include human and animal serum or plasma; urine, tear, sputum or inflammatory exudates (e.g., synovial fluid, cysts, bursas, cerebrospinal fluid, exudates from the thoracic cavity or exudates from the abdominal cavity); any normal or pathological bodily fluid or excretion, including feces or tissue extracts of normal and pathological tissues (e.g., malignant and benign tumors or cancerous tissue); and biopsy material of normal and pathological tissues (e.g., skin, colon, breast, liver, kidney, hair and/or nail). Complex analyte mixtures also include extracts and lysates of bacteria; bacterial, fungal and higher organism composed ecosystems; and extracts or condensates of soil, clouds or air (e.g., exhaled air). Furthermore, complex mixtures of natural origin can be enriched for components with specific features, like proteins or other analytes specific for a disease or a clinically, pathologically or physiologically defined condition, or proteins sharing physico-chemical properties (e.g., charge, mass and/or abundance).

Samples to be screened by the method can also include artificial mixtures of purified or recombinant protein mixes; artificial mixtures of synthetic peptides; artificial mixes of lipids; naturally occurring mixes of organic metabolites; artificial mixes of naturally occurring but enriched or purified organic compounds; and mixes of compounds of synthetic origin and combinations thereof.

In general, complex analyte mixtures and the appropriate controls can be chosen to look for biomarkers having a wide variety of properties and uses. Other uses in addition to those previously mentioned include predicting the bioavailability of a drug, scaling the results from animal models to human subjects, predicting the therapeutic dose in clinical trials, monitoring patient compliance with the treatment modality, identifying patients who have higher likelihood of responding or not responding to a specific treatment, identifying patients who have higher likelihood of expressing or not expressing idiosyncratic reactions, identifying sub-populations of a clinical group and predicting toxicity. Recently, metastatic cells have been observed to contain altered forms of certain proteins present in normal cells. The method of the invention permits the identification of a biomarker even if it is present in an altered form, such as a truncated or alternatively spliced form.

A disease-specific biomarker can be used to identify individuals who, for example, are prone to the disease or condition of interest; show significant genetic susceptibility to a disease or condition of interest; have the disease but in its early asymptomatic stages (e.g., before the actual appearance of the clinically recognizable disease conditions and/or symptoms); are possible responders or non-responders to therapy; or are possible responders with an undesirable reaction (e.g., toxic, allergic, hypersensitivity, nausea, vomiting, changes in EKG, loss of memory, loss of sexual desire, loss of erectile function, loss of kidney function, loss of liver function, lowering of blood pressure and/or elevation of blood pressure). A biomarker may also generally be specific for an individual having any reaction that would limit the administration of a drug or specific to individuals belonging to a group of patients having a certain disease but who form a specific subgroup with characteristic symptoms that require a specific treatment regimen.

Examples of appropriate sources of control samples include healthy individuals who are of the same age and sex and/or who belong to the same race as the donors of the clinical sample; or those who share a genetic background with the donors of the clinical sample, who live in the same or similar environment, who consume the same or similar type of food and who appear apparently healthy. In addition, diseased individuals who share with the diseased group of interest as many as possible of the criteria of same age, same sex, belonging to the same race, living in the same environment and consuming the same type of food, with the exception of the symptom(s) of interest for which a biomarker is to be discovered and developed, would also be suitable controls.

For those embodiments of the invention where the sample (such as serum or plasma) is depleted of abundant components, the principle to be observed is that naturally occurring complex mixtures, e.g., protein mixtures, have a non-identical relative concentration (abundance) of the individual elements comprising the complex mixture. For example, abundant proteins represent an arbitrarily defined class, those that have the highest relative abundance level in any complex mixture. The "highest level" is determined empirically and the term "abundant" is used. For practical purposes, the abundant protein class will have a numeric complexity of less than 5-10% of the total and represent at least 50% of the total mass of protein (or other type of analyte) in any representative sample of the complex mixture.

The abundant class or classes can be removed or just reduced to the concentration range of the rest of the analytes, which are considered to be "low abundance, e.g., proteins." For example, low abundance proteins represent a class of proteins having the lowest relative abundance level in any complex mixture. The "lowest level" is determined empirically and the term "low abundance" is used. For practical purposes, the low abundance protein class may have a numeric complexity of 3,000 to 10,000 or more and usually represent less than 5%-10% of the total mass in any representative sample of the complex mixture.

A systems biology strategy is deployed for prioritization of candidate biomarker hits using a specific data integration concept. This approach is an integrated analysis process of assembling and extracting the essence from divergent items of biological information. The process starts with the identification of primary biomarker candidates that are modified in the process under investigation. In the subsequent steps, attributes for each primary candidate are generated via the collection of additional types of information. These attributes are then expressed in binary, normalized numerical or other computable formats. Finally, values are multiplied by specific weighting factors that are applied empirically based on concepts that drive the prioritization strategy (e.g., ability to be converted into a drug and/or disease relevance). The computed sum of weighted attribute values is used for sorting candidate biomarkers. The final list of candidates undergoes a manual bioanalysis process that evaluates the rationale for having each given candidate on the list one by one and establishes the final priority list.

The invention is also directed to a handheld, light weight, battery operated, point of care, diagnostic device that is applicable to any biologically relevant tests including but not restricted to biomarker discovery and use. The apparatus is capable of carrying out specific biological tests for up to at least a dozen different biomarkers or other potential biological agents in minutes using an integrated microchip in the device that comprises sample preparation, separation and identification compartments. The diagnostic technology is based on specific recognition of antigens by monoclonal antibodies immobilized within the microchannels on the chip in the device. The tests are performed in rapid, high throughput fashion in a capillary or microfluidics chip format taking advantage of the very low or no diffusion limitation inherent with miniaturization. To prevent possible cross contamination the chip can be disposable.

DESCRIPTION OF THE DRAWINGS

Other features and advantages of the present invention will be apparent from the following detailed description of the invention, taken in conjunction with the accompanying drawings of which:

FIGS. 2A and 2B are schematic diagrams of assays appropriate for use in the method according to the invention;

DETAILED DESCRIPTION OF THE INVENTION

Generally, the method of the invention is a rapid integrated, high-throughput, disease-specific monoclonal antibody (mAb)-based biomarker discovery platform that provides new biomarker candidates to accomplish the previously identified objectives. The focus of the invention described herein is on large scale discovery and production of mAb-based, disease-specific clinical assay candidate biomarkers. A desired end outcome of the biomarker discovery process is a highly specific and sensitive assay. In order to ensure the generation of mAb-based, e.g., clinical assay candidates as the outcome of the global (e.g., genome-, proteome- and/or metabolome-wide) biomarker discovery process, the method according to the invention integrates four major technology components: analyte collection, hybridoma screening, nano-volume integrated mass spectrometry (NVIMS) and systematic data analysis and integration.

The classical biomarker research and development process takes about 7-9 years from discovery to approval. The discovery phase of the process is relatively short (e.g., 1-3 years). However, the clinical feasibility phase, assay development, clinical validation, trial test and approval phases can take an additional 6-8 years. The mAb-based platform according to the invention, because it uses clinical samples from a patient pool similar or identical to those patients in clinical trials, can achieve the clinical development and biomarker discovery phase simultaneously and saves up to, for example, 4-6 years of development time. Thus, the mAb-based strategy according to the invention is significantly faster than the classical biomarker discovery and development process.

To eliminate discovery process bottlenecks in the system of the invention and to keep biomarker discovery methods global until the last validation and subsequent development steps, careful consideration is paid to the integration process of divergent but essential genomics, genetics, proteomics, metabolomics and bioinformatics technologies and the information derived from these. A specific integration strategy will result in a large scale delivery of appropriate clinical assay candidates and a robustness in addressing the entire genome, proteome or metabolome.

Figure 1:
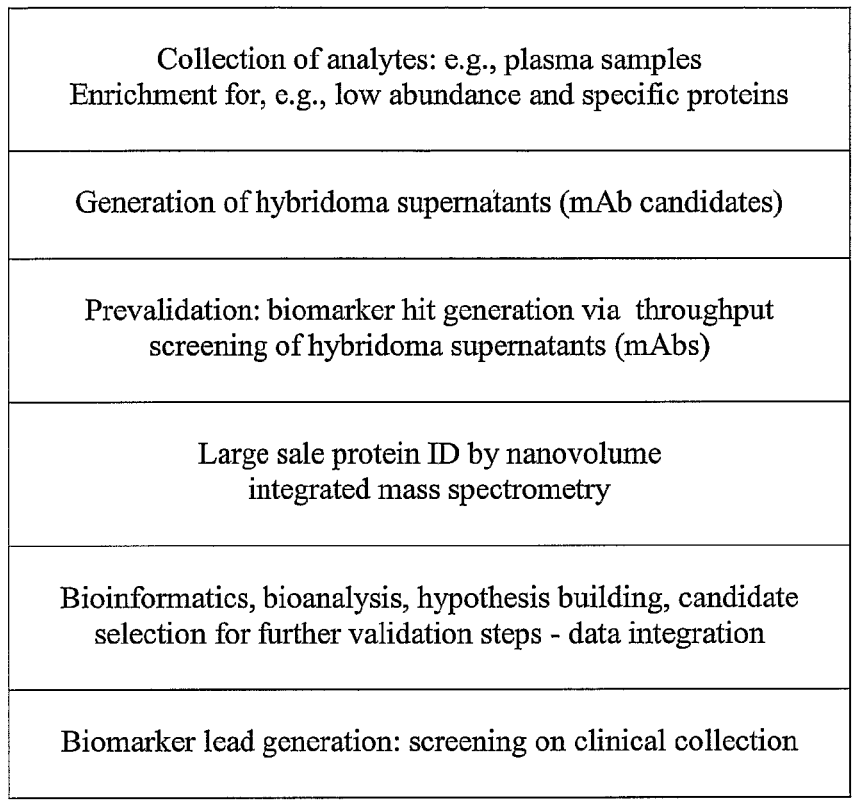
FIG. 1 is a representation of a scheme for a biomarker discovery and development platform according to the invention.

An outline of a preferred embodiment of the platform system according to the invention is given in FIG. 1. This embodiment is designed for the discovery of early disease-specific clinical biomarkers, with the primary goals being (i) to reduce clinical trial length of candidate therapies for chronic diseases and (ii) to predict and follow treatment efficacy of new or marketed drugs. The platform with minor modifications is also applicable to the analysis of non-human samples and problems outside of disease diagnosis and treatment (e.g., ecological, drug and new food product testing and biohazard applications). Depending on the intended application, the complex analyte chosen as a source of potential biomarkers would vary.

The platform of the invention comprises, but is not limited to, the following process steps that are numbered herein as (1) through (6).

(1) Generation of Appropriate Antigens Using an Analyte Collections Approach

Analyte collection achieves the generation of a small set of analyte samples that represent one or multiple diseases or experimental conditions with one or multiple sets of controls. The conditions are chosen to include clinical symptoms and/or disease stages that will have to be predicted by the newly discovered biomarkers before the actual appearance of the disease or condition outcome. The number of individual samples might not exceed 50 in any of the groups. In order to speed the biomarker discovery process, pooled collections could be used at this stage. However, each subject is requested to provide samples for DNA testing.

Sample collection is driven by clinical data and their interpretation, based on the best available medical practice. The resulting inclusion and exclusion criteria are set with physician experts and approved by regulatory bodies.

Enrichment of the collected sample with respect to low abundance and/or disease-specific proteins can be performed based on any desired and suitable biological or physico-chemical characteristics of the targeted complex analyte samples (e.g., concentration and/or mass). A specific two step immunoaffinity absorption strategy, described in detail in Example I, involves (i) depletion of the most abundant proteins (e.g., albumin and immunoglobulins from plasma) from the analyte pool as these proteins are not expected to have biomarker value yet might represent >90% of the total protein and (ii) removal of proteins reacting with polyclonal antisera that are generated to one set of analytes in the pool, for example, the control. The resulting processed sample is, thus, enriched for proteins that were originally present only at low concentration (e.g., <5%-10%) and for proteins that might be present only in one set of the analytes. For enrichment purposes, complex analyte samples can be pooled.

Other enrichment strategies using ligand affinity chromatography or separation technologies that enrich proteins based on their size, charge or binding characteristics to, for example, other proteins can also be used. Furthermore, chemical treatments such as the oxidation of methionine residues may improve the separation of protein properties.

(2) Generation of Hybridoma Supernatants

This step involves well-established technologies aimed at the generation of mAbs to individual components of complex antigen mixes (see, e.g., Kohler G. and Milstein C. Nature 256(5517):495-497, 1975; Burns R. Methods Mol. Biol. 295: 41-54, 2005; Bristol L. A., Romm E., Fintch L. and Takacs L. J. Immunol. 148:332, 1992). The technical steps are as follows: (1) immunization of mice with enriched analyte samples; (2) hybridoma fusion; (3) culturing of fused hybridomas under limiting dilution conditions in microtitre wells; (4) harvesting of hybridoma supernatants; and (5) freezing and storage of hybridoma cells.

(3) Pre-validation: Biomarker Hit Generation Via High-throughput Screening of Hybridoma Supernatants (mAbs) on a First Clinical Collection A well-characterized representative group of individual analyte samples (e.g., 50 plasma samples from patients having a specific disease or disease condition and 50 samples from appropriate control subjects) is selected. A high-throughput assay format is then developed to screen the analyte samples with the mAbs present in hybridoma supernatants.

For example, in a capture micro-ELISA assay, an antibody/antigen reaction is made measurable by immobilization of mAbs and subsequent direct or indirect colorimetric, fluorescent, luminescent or radioactive detection of bound, labeled antigens. Complex analytes can be labeled by biotin, which will allow downstream detection. However, labeling of complex analytes can be achieved by other methods as well.

Biotinylation of a complex analyte sample results in the covalent linkage of biotin molecules to each individual protein or other complex analyte element via terminal and epsilon amino groups or hydroxyl groups. Provided that the biotinylation reaction is performed under saturating conditions, the majority, if not all, of the available terminal and epsilon amino groups or hydroxyl groups will be biotinylated. Consequently, all protein or other complex analyte elements possessing at least one terminal amino group, or both a terminal and an epsilon amino group (i.e., on arginine and lysine residues), or a hydroxyl group will become detectable if bound to the immobilized mAb. After e.g., biotin-N-hydroxy succinimide esterification, virtually all proteins containing at least one reactive site as described will become biotinylated.

Immobilized mAbs will bind to a single antigenic determinant present, usually, on one particular biotinylated protein or biotinylated element of the complex analyte. The specificity of this reaction will permit quantification in the ELISA measurements. First, binding of biotinylated proteins is measured by the use of avidin or streptavidin labeled by enzymes, fluorophores or radioactive elements. A more precise quantification of individual (non-pooled) analyte elements becomes possible by titration of non-biotinylated individual complex analytes against fixed quantities (quasi-saturating conditions) of the biotinylated complex analyte. In this case, dilution factors serve as relative concentration values of individual proteins carrying an antigenic determinant recognized by the immobilized mAb. An example of the ELISA I measurement steps is given below and shown in FIG. 2A.

(i) the IgG from the hybridoma supernatant is captured on microtiter plates by immobilized anti-mouse-IgG-Fc.
(ii) biotinylated pooled enriched complex analyte is used to detect an anti-biomarker reaction.
(iii) non-enriched individual analyte samples are titrated to compete with fixed amounts of candidate biomarker, or a previously determined fixed analyte dilution is used for each individual analyte sample. Percent inhibition is deduced by computing maximal inhibition and assay signal values.

The ELISA reaction described above is then used in a high throughput format to screen all hybridoma supernatants via the following steps.
(i) ELISA I: screen all hybridoma supernatants (e.g., 1000-50,000) against biotinylated complex and pooled analyte mix.
(ii) Select those supernatants that score positive in the assay.
(iii) Determine optimal, sub-saturating conditions for the selected supernatants.
(iv) ELISA II: Test dilutions of individual, non-biotinylated complex analytes in the presence of optimal, sub-saturating amounts of biotinylated pools of complex analyte to determine the 50% inhibitory dilutions that will serve as the relative measures of biomarker concentrations detected by a given mAB present in any individual hybridoma supernatant (FIG. 2B). Alternatively, after initial titration experiments, test the same dilution of all individual analyte samples and determine percent inhibition. The relative inhibition percentage shown in the examples herein was determined by this method.

Screening assays built on other principles than an ELISA can be deployed (e.g., antibody microarrays, high-throughput screening based on MALDI/MS and/or multi-channel capillary electrophoresis). ELISA or microarray data are evaluated, e.g., by published methods. The goal of the data analysis process is the selection of hybridoma supernatants that show the best collection with an important clinical parameter and are specific to one of the analyte groups.

Those hybridoma supernatants that do not give positive results (do not show a "hit") can be saved for screening against another analyte collection. For example, an alternative strategy for mAb-based biomarker discovery is to use large non-redundant mAb libraries for biomarker discovery and screening via sensitive proteomics chips. In this format, complex analyte mixes are derived from the biological source via enrichment. Hybridoma supernatants are generated and antigen identification (ID) is carried out on each mAb containing supernatant. Screening of hybridoma supernatants is stopped when the process saturates and no new antigen IDs are observed. At this stage, a non-redundant set of mAbs is produced in sufficient quantity for further proteomics chip screening. Chips can be constructed by the use of the entire library or by the use of portions of the library that represent specific classes of proteins, e.g. proteins that perform similar function or involved in the development of specific disease processes.

(4) Protein Id by Nanovolume Integrated Mass Spectrometry (NVIMS)

In this step, the small quantity of antibody present in 5-2000 µl hybridoma supernatant is captured, and an advanced high-throughput mass spectrometry based technology is used to identify the antigen to which it binds. Various methods useful in carrying out this step are described in Example II.

Advances in proteomics technologies allow affinity purification of mAbs and the antigen that they recognize on the nano/pico-scale. A ng/pg quantity of mAb can be purified from sub-milliliter amounts of hybridoma supernatants and quasi-equimolar quantities of the antigen can also be purified. Nanovolume scale HPLC/CE columns in boundless or special microfluidics devices or nanowell plate devices can be coupled to high sensitivity FT-MS to achieve high-throughput protein ID, as described in Example II.

(5) Data Integration—Bioinformatics, Bioanalysis, Hypothesis Building/Candidate Selection for Further Validation Steps In this step, data obtained from the platform are analyzed against current medical knowledge and other experimental data available. A systems biology strategy is deployed for prioritization of candidate biomarker hits using a specific data integration concept. This approach is an integrated analysis process of assembling and extracting the essence from divergent biological information (e.g., gene expression analysis, proteomics studies, published information and/or genetic association). The process starts with the identification of primary biomarker candidates from those identified in the mass spectrometry step that qualify because they are: (i) present in, (ii) up or down regulated by, (iii) chemically modified in, or (iv) represent genetic risk to the pathological, physiological or experimental (e.g., drug treatment) process under investigation. In the subsequent steps, attributes for each primary candidate are generated via the collection of additional types of information. These attributes are then expressed in binary, normalized numerical or other computable formats. Finally, values are multiplied by specific weighting factors that are applied empirically based on concepts that drive the prioritization strategy (e.g., ability to be converted into a drug and/or disease relevance). The computed sum of weighted attribute values is used for sorting candidate biomarkers. The final list of candidates undergoes a manual bioanalysis process that evaluates the rationale for having each given candidate on the list one by one and establishes the final priority list.

Data integration is achieved via the following steps:
(i) Input a file featuring a single column corresponding to a unique and unambiguous transcriptional unit identifier; the method manages splice variants of any given genes as distinct transcriptional unit data objects;
(ii) To this input file are joined properties of the polypeptide/analyte specified by the transcriptional unit (known biochemical activity, Prosite and pFam motifs, cellular location, known cellular translocation events happening in response to either an internal or external clue (e.g., nuclear receptor hormones); most of these attributes are categorical data types;
(iii) To this matrix is joined an additional series of fields featuring data sets captured from whole gene sets expression profiling assays, quantitative proteomics, in situ hybridization, immunocyto-localization, ChIP-on-chip technology, and protein-protein interaction assays; each attribute has its own data type and represents a given quantity, categorical, numerical, discrete or continuous, binomial, etc.
(iv) From each of these initial attribute values is derived a "meta" value that weights the relevance of the given attribute to the query (example of a query: in the instance of a inflammatory reaction in response to an airborne allergen, what are the gene products most likely to be found in the vascular system surrounding the bronchioles?). For some questions, there is some precedent knowledge, which is used to tune up the parameters used to derive the "meta" values from the original attribute values of the matrix such that the query returns the expected outcome for the known occurrence of the query. In other instances, such prior knowledge is not available (e.g., what are the cellular polypeptides released in the plasma in patients entering the initial phase of a given disease). Data captured by the Monoclonal Antibody Based Biomarker Discovery and Development Platform according to the invention are aimed at setting the appropriate parameters for deriving the "meta" values of the attributes. The ranking is based on either arithmetically or geometrically combining the meta values. The outcome is a sorted list with the most likely candidate ranked on the top.

In summary, prioritization concepts are driven by biomarker need (e.g., response to treatment, disease progression, disease improvement and/or toxicity) and available data on specificity and sensitivity of the mAb-based assays. Then, bioanalysis is used to examine the top candidates one by one. If the data analysis is carried out in parallel with the screening and antigen ID steps, the bioanalysis step will select candidates for which screening assays can be repeated against individual samples for the generation of higher statistical confidence level mAb-based candidates.

(6) Biomarker Lead Generation: Screening on an Extended Clinical Collection

In order to progress to a biomarker lead candidate and to generate data for the early biomarker development steps, a second discovery level validation step is deployed, which is performed on a larger analyte collection, typically 250 individual samples (e.g., patients or subjects) in each group. Exclusion and inclusion criteria are designed by clinical need (e.g., response or reaction to a drug treatment, improvement in a disease state, diagnosis of a disease etc.) and by epidemiologic data, if available. In the same manner as for the first clinical collection, each subject is requested to provide samples for DNA testing.

For the development of mAb assays that can be used on large cohorts and in clinical trials, a robust, mAb-based, research-level clinical assay is needed that shows a sufficient level of reproducibility, sensitivity and specificity. This assay is developed as a single ELISA-like or other single mAb-based assay or as an assay multiplexed from various mAbs or from various platforms such as, for example, qPCR, SNP or genotyping. In order to progress to this step(s), hybridomas will have to be cloned and mAbs will have to be produced on a large scale via classical methods know to those persons skilled in the art.

The examples described herein are provided to illustrate advantages of the present invention that have not been previously described and also to assist a person of ordinary skill within the art in performing the method according to the invention. The examples can include or incorporate any of the variations or embodiments of the invention described above. The following examples are not intended in any way to otherwise limit the disclosure.

EXAMPLE I

Enrichment for Low Abundance and/or Disease Process Specific Proteins, Generation of Hybridoma Supernatants and Screening A complex protein mix of human origin is collected from groups of subjects that are identified (e.g., by clinical tests) as having a common trait or condition. These groups may represent, for example, any of the variations described above. Pools of samples are prepared by mixing equal volumes of samples (e.g., plasma or serum from the individual patients).

Abundant proteins are then depleted from individual pools via a two-step affinity chromatography procedure so that antibodies can be generated to the low abundancy or low level proteins in the pool. These have a greater likelihood of being of diagnostic interest and of having biomarker potential. The first depletion step uses column chromatography against immobilized antibodies or ligands having specific affinity to a few of the most abundant proteins typically found in the type of sample being analyzed. This approach has typically achieved a 10-fold enrichment of the mixture for low level proteins. The flow through from this column, the "first cleared mix," is collected and subjected to the second step of separation.

In the second affinity chromatography step, the first cleared mix is loaded onto a column containing, for example, immobilized polyclonal antibody prepared against the complex analyte mix control (e.g., serum or plasma proteins) or against one of the specific pools that are being compared; or immobilized antibody representing a mix of, e.g., 20-500 monoclonal antibodies to specific components of the complex protein mix. The flow through of this column, the "second cleared mix," is collected.

This two step approach, initial depletion steps using targeted ligands followed by a polyclonal antibody column against other antigens in the control mix, achieves a much more complete depletion of abundant proteins. The depletion process is monitored by, for example, 1D or 2D gel electrophoresis and LC/MS analysis. Analysis of the second cleared mix shows that the analyte population has been enriched more than 20-fold for proteins that were less abundant in the original sample.

For this example, the complex analyte to be screened was chosen so as to look for biomarker candidates that show a relationship to chronic obstructive pulmonary disease (COPD). Smoking COPD patients were carefully selected to represent a homogeneous clinical group that had no other apparent inflammatory disease or condition. Lung function tests (<80% FEV1 measured/predicted) drove the selection criteria. Smoking age and sex matched controls, individuals who displayed apparently normal lung function tests (e.g., >80% FEV1 measured/predicted), were also selected.

Generation of hybridoma supernatants following immunization resulted in the generation of more than 3000 individual antibody-producing hybridomas. A first level screening against the pooled analyte sample identified 250 hits. These were reduced to 10 high quality candidate mAbs in subsequent confirmatory screening. The screening results for three of these candidates are given in FIGS. 3, 4 and 5.

Figure 3:
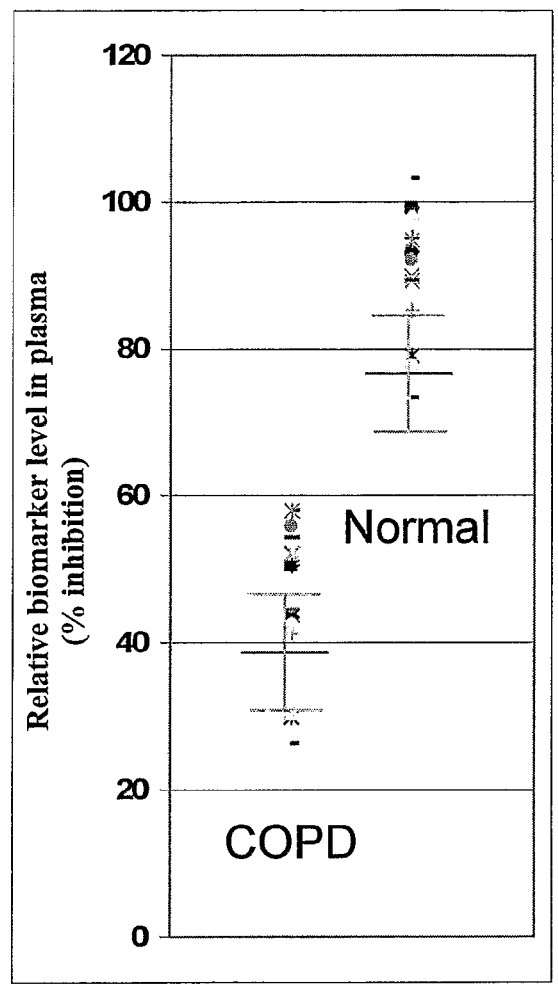
FIG. 3, a plot of relative biomarker levels in plasma for normal and chronic obstructive pulmonary disease (COPD) subjects, represents the screening results for one candidate biomarker discovered by the method of the invention.

FIG. 3 shows the results of an inhibition assay carried out with patient plasma protein at a concentration of 8 μg/ml using cleared normal biotinylated plasma protein. As can be seen in FIG. 3, this test clearly differentiates 18 COPD plasma samples from 18 normal plasma samples with no data overlaps between the two groups. The results show a mean COPD relative biomarker ELISA percent inhibition value of 45.65 (SD+/−9.47) and mean normal relative biomarker ELISA percent inhibition value of 89.57 (SD+/−8.93). The results were determined to be significant with the Student's paired T test. P value=<0.0001; here, the p values were obtained with the Mann Whitney test, which is insensitive to group inhomogeneity.

Figure 4:
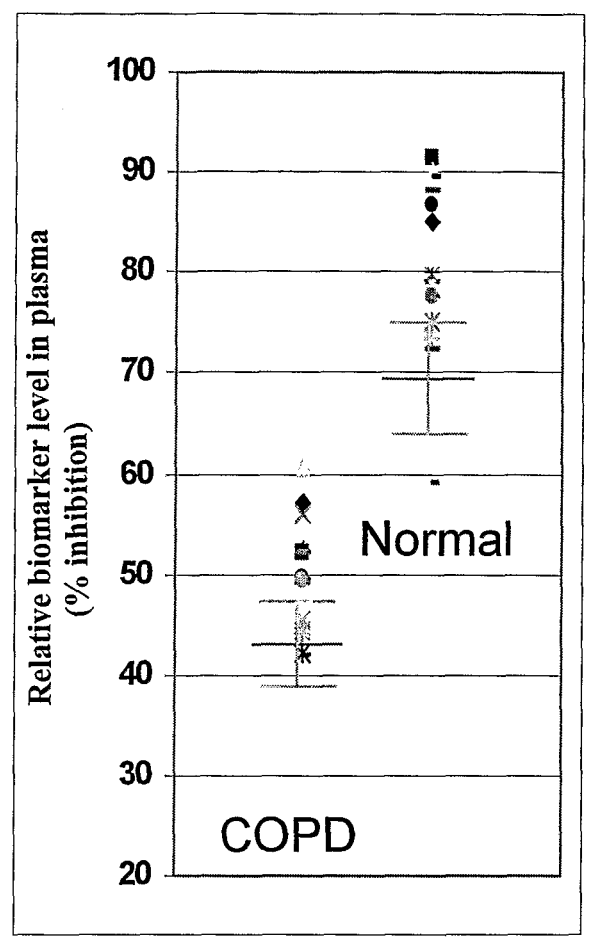
FIG. 4, a plot of relative biomarker levels in plasma for normal and COPD subjects, represents the screening results for a second candidate biomarker.

FIG. 4 shows the results with a different candidate mAb using 40 μg/ml of patient plasma protein. As can be seen, this test differentiated 18 COPD plasma samples from the majority of 18 normal plasma samples. The results show a mean COPD relative biomarker percent inhibition level of 48.42 (SD+/−6.45) and a mean normal relative percent inhibition value of 79.70 (SD+/−8.02). Again, p=<0.0001.

Figure 5:
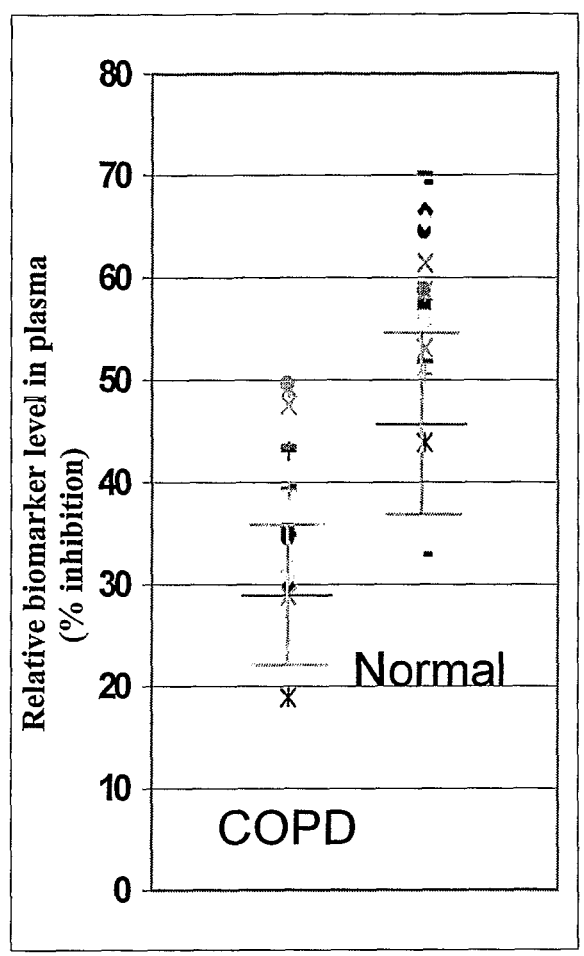
FIG. 5, a plot of relative biomarker levels in plasma for normal and COPD subjects, represents the screening results for a third candidate biomarker.

The results for the third candidate mAb are given in FIG. 5. This test differentiated the majority of 24 COPD plasma samples from the majority of 25 normal plasma samples with a p value (Mann Whitney)=<0.0001. This statistical assay was used because it does not assume normal (or any particular) distribution of group data sets and eliminates the outlier data points.

EXAMPLE II

Large Scale Protein (Antigen) Purification and Identification

This example describes the preparation of an industrial scale process based on existing technology demonstrating the use of mass spectrometry for hybridoma characterization. This improved industrial scale process couples different devices that allow high-throughput manipulations (e.g., microfluidics chips, nanowells and/or individual or bundled capillaries) to sensitive mass spectrometer(s) such as FT-MS. The process of the invention requires significantly less mAb for antigen identification than prior art processes due to miniaturization of the analytical device.

In the method described herein, capillaries, nanowells and/or microchips are sequentially arranged as functional units/surfaces that: (i) bind and concentrate 0.1-100 μg mAb specifically via the Fc portion and allow the rest of the hybridoma supernatant to exit the system; (ii) allow micro/nano-scale affinity binding and elution of individual analyte species to/from the mAb(s) present in individual hybridoma supernatants and, thus, allow elution and concentration of affinity purified quasi-homogeneous analyte species from complex analyte protein mixtures; (iii) digest the concentrated homogeneous analyte species with appropriate proteolytic enzyme(s) (e.g., trypsin) for subsequent MS analysis; and (iv) allow easy processing of the digested analyte for loading onto a mass spectrometer.

Samples at this stage are transited to a specific coupling and loading unit that injects the sample into the mass spectrometer for analysis. In this way, the sequential identification of each individual fragment from a digested affinity purified analyte species and the identification of the mass of the fragments permits high fidelity protein ID assignment with the use of current empiric and predicted protein data sets.

Generation of bioactive solid surfaces through immobilization of antibodies is important for biomarker discovery and screening. The solid-phase environment provides sufficient bioactivity, stability and reproducibility without a high background or loss of antigens. The progress in microfabrication technologies and the trend towards the creation of integrated biodevices imposes a new and major constrain on immobilization techniques, for example, the requirement for highly defined space-programming of the immobilization of biomolecules. In this process, anti-mouse IgG heavy chain Ab or protein G will be bonded, for example, onto the silica surfaces of microbore capillaries or microfluidics channels or the siloxane surfaces of nanowells to form highly controlled affinity surfaces. These will be used in high-throughput screening (HTS) processes with no diffusion limitation.

There are two possible approaches to address this task: a flexible "lego-like" approach using pieces of microbore capillary columns connected to each other via relevant valve structures or an integrated monolithic approach by microfabrication. In both instances, there are three major parts of the assembly: (i) an immunoaffinity trapping chamber connected to (ii) a digestion chamber that is connected to (iii) a high-resolution mass spectrometer. If necessary, a separation column can be inserted between the immunoaffinity trapping chamber and the digestion chamber. Other configurations would also be comtemplated by a person of ordinary skill. The inner wall of the immunoaffinity trapping chamber is covered, e.g., by covalently attached anti-mouse IgG heavy chain Ab or protein G. In order to increase the reaction surface, beads can be used in microcapillaries or microfabricated poles or other structures can be used in microfluidics devices.

Figure 6:
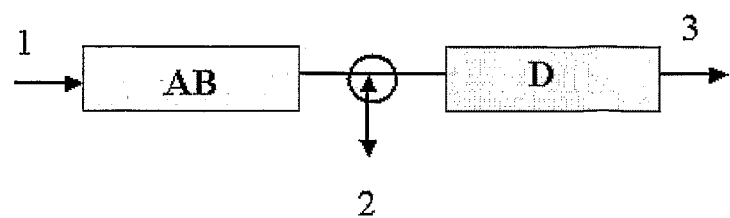
FIG. 6 is a representation of a high-throughput screening system according to the invention.

FIG. 6 is a schematic of the process steps. Referring to FIG. 6, the background in the hybridoma supernatant is assessed by flushing the supernatant through the immunoaffinity trapping chamber to saturate the affinity surface with IgG (1→AB→2). The chamber (AB) contains the immobilized immunoaffinity trapping agent (e.g., anti-mouse IgG heavy chain or protein G). Next, the trapped IgGs are washed with phosphate buffered saline (PBS) (1→AB→2) and then eluted with an acidic buffer system into the digestion chamber. The pH is adjusted through outlet 2 during the transfer (mixing). In a similar manner to the covalent coating of the immunoaffinity trapping chamber, the inner wall of the digestion chamber is covalently covered by an appropriate enzyme (e.g., trypsin) and the reaction surface can also be increased, as described above, by using beads in microcapillaries or microfabricated poles in microfluidics devices. After complete digestion, the digested sample is transferred from exit port 3 and subjected to MS/MS or μLC-MS/MS analysis (D→3).

In high-throughput screening mode, the affinity surface of the immunoaffinity trapping chamber is first saturated by the IgG from the hybridoma supernatant (1→AB→2). This step is followed by perfusion with the antigen mixture (1→AB→2). Then, the chamber is washed with PBS (1→AB→2), and the IgG-antigen complex is eluted with an acidic elution buffer into the digestion chamber (D). The pH is adjusted through outlet 2 during the transfer (mixing). After complete digestion, the digested sample is subject to MS/MS or μLC-MS/MS analysis (D→3).

Besides running separate background determination and high-throughput screening steps as described above and deconvoluting the results by computer, another strategy can involve separation of the digestion product of the background determination and the screening steps by a serially connected HPLC column. In this latter instance, the non-identical peaks are collected and subjected to MS/MS or μLC-MS/MS analysis.

Figure 7:
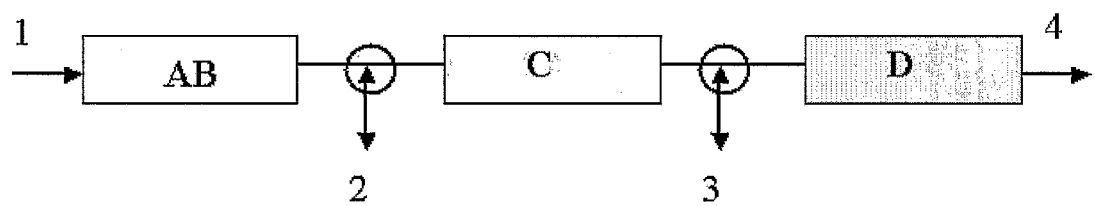
FIG. 7 is a representation of a high-throughput screening system according to the invention.

A different strategy, shown in FIG. 7, involves HPLC separation between the two chambers (i.e., only the non-identical peaks are digested and injected to the MS/MS or μLC-MS/MS system). The system shown in FIG. 7 can include a separation column (C) in between the two chambers (AB) and (D) so that the IgG peak can go to waste through channel 3, and the peak representing the antigen can go into the digestion chamber (C→D) and, subsequently, to MS/MS or μLC-MS/MS analysis through channel 4.

Figure 8:
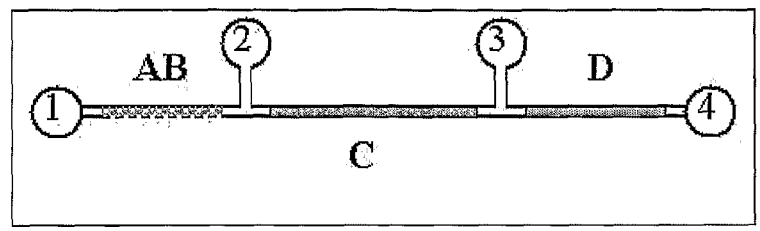
FIG. 8 is a representation of a high-throughput screening system according to the invention.

Alternatively, the same methods can be practiced in a monolithic microfluidics device, either in a single channel (FIG. 8) or in parallel channels such as 96, 384, 1536 lane structures modeled on the channel shown in FIG. 8.

The hybridoma supernatants (mAbs) that are determined to have high specificity and good binding properties and that discriminate sets of samples with acceptable confidence levels are selected for individual mAb mediated clinical assay development. The resulting assays are then used for large-scale validation of biomarkers in patient samples in large cross-sectional studies, for example, validation of earlier analyzed collections, and longitudinal clinical studies, for example, clinical trials.

In another method, large scale protein screening is carried out using nanowell polydimethylsiloxane (PDMS) plates with immobilized linkers in each well (e.g., using avidin, protein A, Protein G and/or specific anti-Ig heavy chain) capable of high-throughput screening of complex analytes (e.g., full plasma proteins or purified disease-specific low abundance proteins). The binding assay is accomplished in the nanowells. After all non-specific and unbonded material is washed out, the binding linker is cleaved. The released proteins are digested either in situ for nano-ESI/MS (e.g., nanomate) or transferred to a digestion enzyme-containing membrane that will act as MALDI plate for MS interrogation. To increase precision and detection limit, two or more parallel wells can be used, one for the binding measurement with a reporter only (e.g., fluorescence) the other being used for digestion and MS analysis.

Nano-ELISA involves protein A, protein G or gamma Ig being immobilized in the nanowells. During the screening reaction, the immunoglobulin binds to the immobilized linker and then is available to bind the candidate biomarker from the complex analyte sample (e.g., plasma or pooled plasma, "cleared plasma" or pooled cleared plasma).

A screening assay to identify hybridoma supernatants that react with pooled complex analyte mixtures uses biotinylated complex analyte (e.g., total plasma proteins or pooled and depleted cleared plasma and/or plasma mixtures). If binding is detected, a biomarker hit has been identified.

In semi-quantitative differential screenings, two or more samples of complex analyte pools are compared. For example, pooled total plasma protein or pooled low abundance protein, from a point of care assay and a control, both biotinylated, could be compared. Detection of a signal intensity difference identifies a biomarker hit.

A quantitative screening assay of individual complex analyte samples builds on the first assay. Non-biotinylated individual complex analyte samples are titrated and described but this time, only a selected set of hybridoma supernatants are screened, those that were identified as hits in the first assay. Titration curves provide quantitative measure of specific antigen concentration in each individual analyte sample. IC50 values will be used for comparison and statistical analysis of the entire tested set of individual complex analytes (e.g., a set of 50 disease plasma samples) will be compared to a set of healthy control plasma samples.

Detection can be by, for example, fluorescence, radioactive, calorimetric, proximity or enzymatic techniques as appropriate. In the example described herein, avidin-biotin-peroxidase (ABC) complexes are used to measure binding or binding and competition of biotinylated complex analyte samples as would be appropriate.

Parallel microwells or microfabricated microfluidics devices are used for protein ID. Loading of purified protein for ID to MALDI is electronically or manually driven by screening results and performed accordingly (e.g., on all hits).

EXAMPLE III

Hand-held Point of Care Device

A handheld, light weight, battery operated, point of care, diagnostic device is being developed that is applicable to any biologically relevant tests, including but not restricted to biomarker discovery and use. The apparatus runs specific biological tests for up to at least a dozen different biomarkers or other potential biological agents in minutes using an integrated microchip in the device that comprises sample preparation, separation and identification compartments. The diagnostic technology is based on specific recognition of antigens by monoclonal antibodies immobilized within the microchannels on the chip in the device. The tests are performed in rapid, high throughput fashion in a capillary or microfluidics chip format taking advantage of the very low or no diffusion limitation inherent with miniaturization. To prevent possible cross contamination the chip can be disposable.

Figure 9:
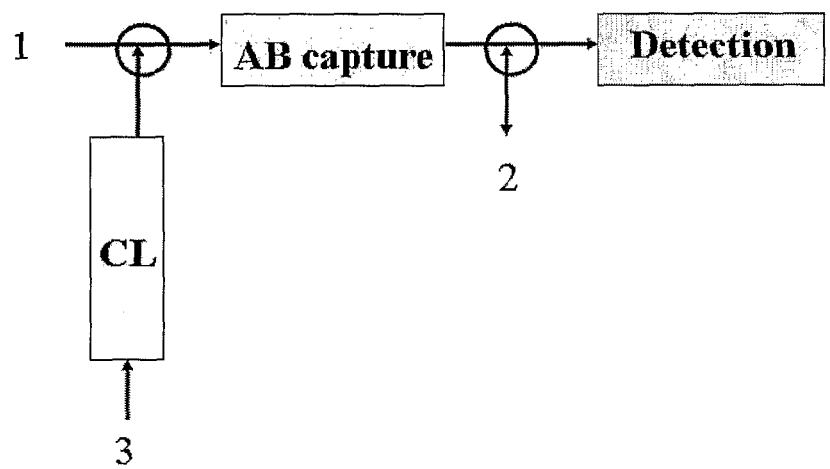
FIG. 9 is a schematic representation of the processes carried out using an integrated microchip in a handheld, point of care, diagnostic device according to the invention.
Figure 10:
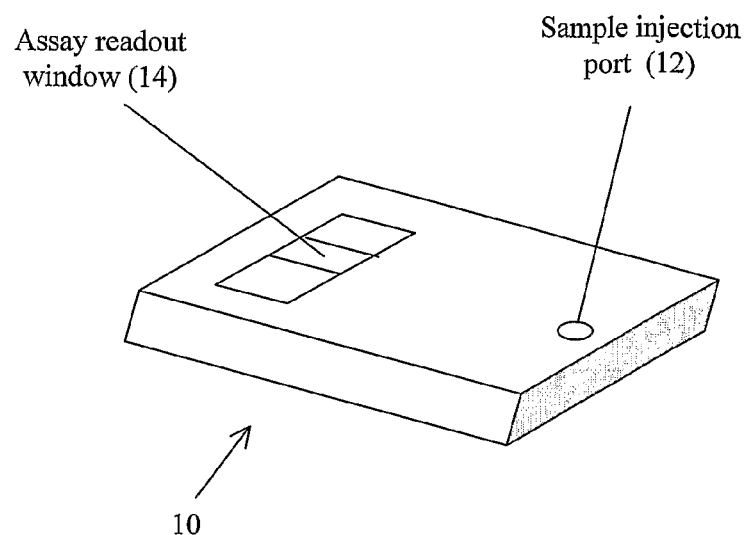
FIG. 10 is a perspective view of a handheld, point of care, diagnostic device according to the invention.

Referring to FIG. 10, an exemplary point of care device according to the invention (10) includes a sample injection port (12) and an assay readout window (14). Referring to FIG. 9, a schematic representation of the processes carried out using the device shown in FIG. 10 and the mode of operation of channels and compartments within the device is given. that uses miniaturized detection methods can be readily used during clinical trials in HTS mode. In high throughput screening mode, the affinity surface of the immunoaffinity trapping chamber (AB capture) is first saturated by the IgG from the hybridoma supernatant of choice. The non-adsorbed material exits the assay channel at waste port 2 (1=>AB capture=>2). This step is followed by perfusion with the sample (e.g., plasma). The sample in this case is driven into the immunoaffinity trapping chamber (AB capture) through a sample processing compartment (CL) in order to remove particles and components that may disturb proper affinity capture. Again, the effluent is eliminated at waste port 2 (3=>AB capture=>2). Then, chamber AB capture is washed with PBS (1=>AB capture=>2), and the IgG-antigen complex is eluted with an acidic elution buffer into a detection chamber (1=>AB capture=>Detection). Detection is accomplished by miniaturized methods according to established procedures, e.g., by fluorescence, radioactive, calorimetric, proximity or enzymatic techniques as appropriate. In the example described herein, avidin/biotin-peroxidase (ABC) complexes (Vector) are used to measure binding or binding and competition of biotinylated complex analyte samples, as appropriate with a high throughput manner. Alternatively multichannel capillary electrophoresis can be employed with mAb capture feature and fluorescent or chemiluminescent detection technology.

While the present invention has been described in conjunction with a preferred embodiment, a person of ordinary skill within the art, after reading the foregoing specification, will be able to effect various changes, substitutions of equivalents and other alterations to the invention set forth herein. The embodiments described above may also each include or incorporate any of the variations of all other embodiments. It is therefore intended that the protection granted by Letter Patent hereon be limited only by the definitions contained in the appended claims and equivalents thereof.

What is claimed is:

1. A method of biomarker discovery, said method comprising the steps of:
    providing a complex analyte mixture sample, said sample comprising proteins and peptides, as a candidate biomarker source, said complex analyte mixture sample being depleted of proteins that are less than 10% of the total number, and simultaneously represent at least 50% of the total mass, of proteins and peptides in said sample, said depleted proteins and peptides being denominated abundant proteins;
    providing a control sample for said complex analyte mixture sample;
    injecting a model animal with an aliquot of said abundant protein-depleted complex analyte mixture sample as an immunogen so as to generate, from individual hybridoma cell lines, a population of monoclonal antibodies directed against antigens in said complex analyte mixture sample;
    screening said population of monoclonal antibodies directed against antigens in said complex analyte mixture sample against another aliquot of said complex analyte mixture sample;
    screening said population of monoclonal antibodies directed against antigens in said complex analyte mixture sample against an aliquot of said control sample; and
    selecting at least one monoclonal antibody that exhibits a statistically significant difference in binding to an antigen in said complex analyte mixture sample compared to an antigen in said control sample, whereby the antigen(s) selectively bound by said at least one selected monoclonal antibody are said biomarker(s).

2. The method of claim 1, wherein, in said selecting step, said one or more monoclonal antibodies exhibits an increase in binding to an antigen in said complex analyte mixture sample compared to an antigen in said control sample.

3. The method of claim 1, wherein, in said selecting step, said one or more monoclonal antibodies exhibits a decrease in binding to an antigen in said complex analyte mixture sample compared to an antigen in said control sample.

4. The method of claim 1, wherein said complex analyte mixture sample is diluted before use as an immunogen.

5. The method of claim 1, wherein said complex analyte mixture sample is depleted of abundant proteins by fractionation before use as an immunogen.

6. The method of claim 1, wherein said complex analyte mixture sample is a clinical sample.

7. The method of claim 6, wherein said complex analyte mixture sample is a human bodily fluid.

8. The method of claim 7, wherein said complex analyte mixture sample is human blood.

9. The method of claim 8, wherein said complex analyte mixture sample is human plasma.

10. The method of claim 8, wherein said complex analyte mixture sample is human serum.

11. The method of claim 7, wherein said complex analyte mixture sample is human urine.

12. The method of claim 7, wherein said complex analyte mixture sample is human cerebrospinal fluid.

13. The method of claim 1, wherein said complex analyte mixture sample comprises glycoconjugated proteins or peptides.

14. The method of claim 1, wherein said complex analyte mixture sample comprises a group of disease specific proteins.

15. The method of claim 1, wherein said complex analyte mixture sample is enriched in a class of analyte elements before use as an immunogen.

16. The method of claim 6, wherein said complex analyte mixture sample is from an individual patient, wherein said control sample is from one or more healthy individuals and whereby said selecting step identifies a biomarker that distinguishes said patient from said healthy individuals.

17. The method of claim 6, wherein said complex analyte mixture sample is from an asymptomatic individual having increased risk for the disease of interest, wherein said control sample is from one or more healthy individuals and whereby said selecting step identifies a biomarker that distinguishes said asymptomatic individual from said healthy individuals.

18. The method of claim 6, wherein said complex analyte mixture sample is from an individual patient who has responded to a treatment, wherein said control sample is from an individual patient who has not responded to said treatment and whereby said selecting step identifies a biomarker that distinguishes an individual patient who will respond to said treatment from an individual patient who will not respond to said treatment.

19. The method of claim 1, further comprising the step of determining the identity of said biomarker(s).

20. The method of claim 1, further comprising the steps of determining the identity of a plurality of said biomarkers.

21. A method of biomarker discovery, said method comprising the steps of:
    providing a complex analyte mixture sample, said sample comprising proteins and peptides, as a candidate biomarker source, said complex analyte mixture sample being depleted of proteins that are less than 10% of the total number, and simultaneously represent at least 50% of the total mass, of proteins and peptides in said sample, said depleted proteins and peptides being denominated abundant proteins;
    providing a control sample for said complex analyte mixture sample;
    injecting a model animal with an aliquot of said abundant protein-depleted complex analyte mixture sample as an immunogen so as to generate, from individual hybridoma cell lines, a population of monoclonal antibodies directed against antigens in said complex analyte mixture sample;

screening said population of monoclonal antibodies directed against antigens in said complex analyte mixture sample against another aliquot of said complex analyte mixture sample;

screening said population of monoclonal antibodies directed against antigens in said complex analyte mixture sample against an aliquot of said control sample;

selecting a plurality of monoclonal antibodies that each exhibits a statistically significant difference in binding to an antigen in said complex analyte mixture sample compared to an antigen in said control sample, whereby the antigens selectively bound by said plurality of selected monoclonal antibodies are a plurality of said biomarkers; and determining the identity of said plurality of biomarkers.

22. A method of generating a monoclonal antibody library related to a disease or condition, said method comprising the steps of:

providing a complex analyte mixture sample related to a disease or condition, said sample comprising proteins and peptides, as a candidate biomarker source, said complex analyte mixture sample being depleted of proteins that are less than 10% of the total number, and simultaneously represent at least 50% of the total mass, of proteins and peptides in said sample, said depleted proteins and peptides being denominated abundant proteins;

providing a control sample for said complex analyte mixture sample;

injecting a model animal with an aliquot of said abundant protein-depleted complex analyte mixture sample as an immunogen so as to generate, from individual hybridoma cell lines, a population of monoclonal antibodies directed against antigens in said complex analyte mixture sample ;

screening said population of monoclonal antibodies directed against antigens in said complex analyte mixture sample against another aliquot of said complex analyte mixture sample;

screening said population of monoclonal antibodies directed against antigens in said complex analyte mixture sample against an aliquot of said control sample; and selecting a plurality of monoclonal antibodies that each exhibits a significant difference in binding to an antigen in said complex analyte mixture sample compared to an antigen in said control sample, whereby the plurality of monoclonal antibodies selected as exhibiting a significant difference in binding to an antigen in said complex analyte mixture sample compared to an antigen in said control sample is said monoclonal antibody library related to said disease or condition.

23. A method of biomarker discovery, said method comprising the steps of:

providing a complex analyte mixture sample, said sample comprising proteins and peptides, as a candidate biomarker source, wherein said complex analyte mixture sample is related to a biological process of interest;

providing a control sample for said complex analyte mixture sample;

depleting said complex analyte of one or more proteins that are less than 10% of the total number, and simultaneously represent at least 50% of the total mass, of proteins and peptides in said sample, said depleted proteins and peptides being denominated abundant proteins;

injecting a model animal with an aliquot of said abundant protein-depleted complex analyte mixture sample as an immunogen so as to generate, from individual hybridoma cell-lines, a population of monoclonal antibodies directed against antigens in said complex analyte mixture sample;

screening said population of monoclonal antibodies directed against antigens in said complex analyte mixture sample against another aliquot of said complex analyte mixture sample;

screening said population of monoclonal antibodies directed against antigens in said complex analyte mixture sample against an aliquot of said control sample;

selecting a plurality of monoclonal antibodies that each exhibits a statistically significant difference in binding to an antigen in said complex analyte mixture sample compared to an antigen in said control sample, whereby the antigens selectively bound by said plurality of selected monoclonal antibodies are a plurality of said candidate biomarkers;

determining the identity of said plurality of biomarkers; and identifying individual biomarkers among said plurality of biomarkers that are associated with specific changes in said biological process of interest.

24. The method of claim 6, wherein said complex analyte mixture sample is from two or more individual patients.

25. A method of biomarker discovery, said method comprising the steps of:

providing a human bodily fluid sample, said sample comprising proteins and peptides, as a candidate biomarker source, said human bodily fluid sample being depleted of proteins that are less than 5-10% of the total number, and simultaneously represent at least 50% of the total mass, of proteins and peptides in said sample;

providing a control sample for said human bodily fluid sample;

injecting a model animal with an aliquot of said abundant protein-depleted human bodily fluid sample as an immunogen so as to generate, from individual hybridoma cell lines, a population of monoclonal antibodies directed against antigens in said human bodily fluid sample;

screening said population of monoclonal antibodies directed against antigens in said human bodily fluid sample against another aliquot of said human bodily fluid sample;

screening said population of monoclonal antibodies directed against antigens in said human bodily fluid sample against an aliquot of said control sample; and selecting at least one monoclonal antibody that exhibits a statistically significant difference in binding to an antigen in said human bodily fluid sample compared to an antigen in said control sample, whereby the antigen(s) selectively bound by said at least one selected monoclonal antibody are said candidate biomarker(s).

* * * * *

UNITED STATES PATENT AND TRADEMARK OFFICE
CERTIFICATE OF CORRECTION

PATENT NO.         : 8,512,959 B2
APPLICATION NO.    : 10/588392
DATED              : August 20, 2013
INVENTOR(S)        : Laszlo Takacs et al.

Page 1 of 1

It is certified that error appears in the above-identified patent and that said Letters Patent is hereby corrected as shown below:

On the title page item [73] should read as shown below:

Northeastern University, Boston, MA (US)

Signed and Sealed this
Fifteenth Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,512,959 B2  
APPLICATION NO. : 10/588392  
DATED : August 20, 2013  
INVENTOR(S) : Laszlo Takacs et al.

Page 1 of 1

It is certified that error appears in the above-identified patent and that said Letters Patent is hereby corrected as shown below:

In the Specification

Column 1, Line 14, insert the following:  
--STATEMENT REGARDING FEDERALLY SPONSORED RESEARCH OR DEVELOPMENT  
This invention was made with government support under Grant Number GM015847 awarded by the National Institutes of Health. The government has certain rights in the invention.--

Signed and Sealed this  
Fifteenth Day of December, 2020

Andrei Iancu  
*Director of the United States Patent and Trademark Office*